United States Patent [19]

Kabanek

[11] Patent Number: 5,560,375
[45] Date of Patent: Oct. 1, 1996

[54] PATIENT'S HAND IMMOBILIZER

[76] Inventor: Joseph R. Kabanek, 32390 IH-10 West, Boerne, Tex. 78006

[21] Appl. No.: 551,475
[22] Filed: Nov. 1, 1995
[51] Int. Cl.⁶ ...................................................... A61F 5/37
[52] U.S. Cl. ............................................ 128/878; 128/879
[58] Field of Search .................................... 128/845, 846, 128/869, 877, 878, 879; 602/5, 20, 21, 22; 2/16, 21, 160

[56]  References Cited

U.S. PATENT DOCUMENTS

| | | | |
|---|---|---|---|
| 1,867,258 | 7/1932 | Fruehauf | 602/22 |
| 2,863,449 | 12/1958 | Spencer | 602/21 |
| 5,113,849 | 5/1992 | Kuiken | 602/21 |
| 5,205,812 | 4/1993 | Wasserman | 128/878 |
| 5,282,483 | 2/1994 | Wang | 128/882 |

Primary Examiner—Michael A. Brown
Attorney, Agent, or Firm—Paul H. Gallagher

[57]  ABSTRACT

A main panel of aluminum shaped to the hand, with side tab segments for bending over the wrist and the main part of the hand. It includes a layer of sponge material glued to the aluminum layer.

3 Claims, 2 Drawing Sheets

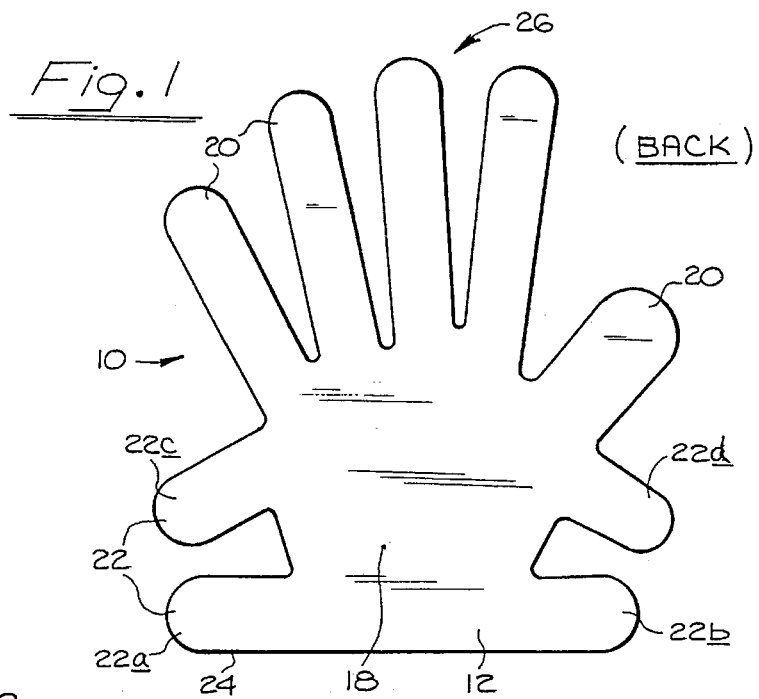
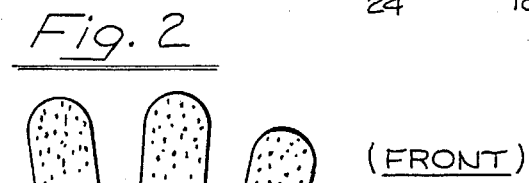
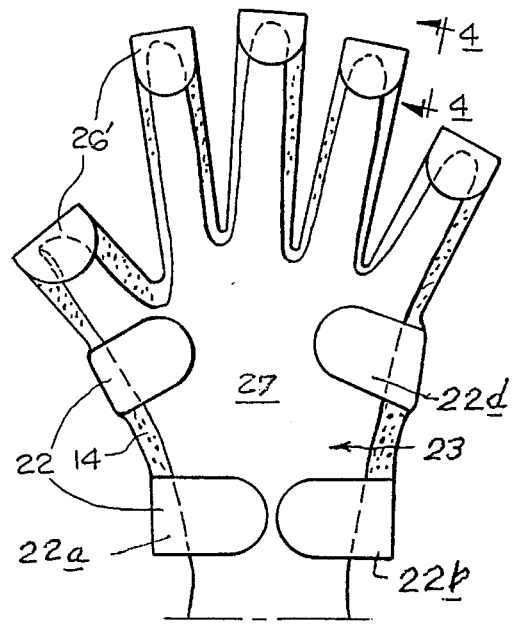
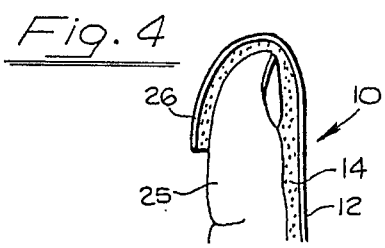

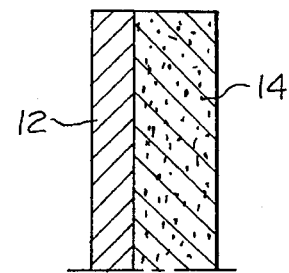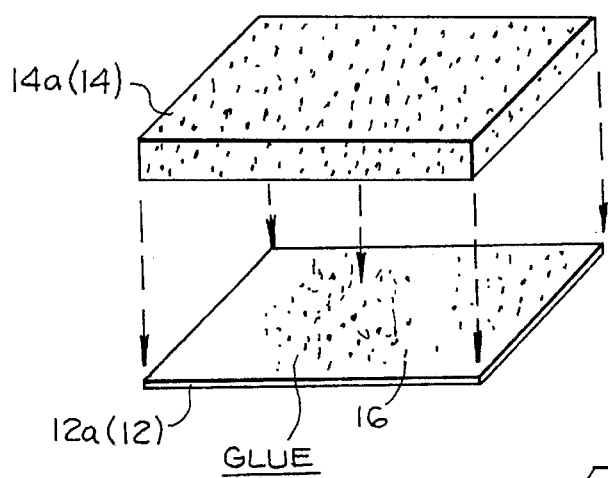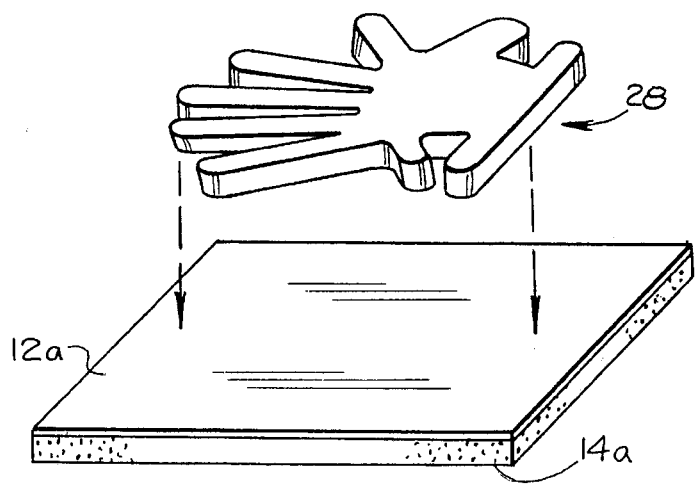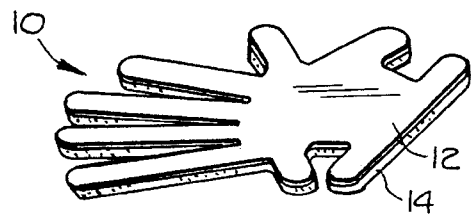

5,560,375

PATIENT'S HAND IMMOBILIZER

SUMMARY OF THE INVENTION

When a patient is given anesthesia for purposes of an operation, various reactions occur in his body, including one in which the hands tend to double up or clinch. Immobilizers are applied to the hands and they grip the fingers in a certain way to keep the hands from doubling up. Such an immobilizer is in the form generally of the shape of the hand, with digit elements corresponding to the fingers and having other elements forming tabs which are bent over onto the fingers for holding the fingers straight, and for holding the device on the hand. Heretofore such immobilizers were made of lead, but lead has proved to be disadvantageous in a number of ways, including fabrication of them, applying them to the hand, and what is most serious, particles of the lead find their way on or into the hands of the patient, and additionally onto the hands or clothes of the staff.

A principal object of the invention is to provide a patient's hand immobilizer made of aluminum, with a cushion combined with the aluminum to form a more comfortable grip on the hand.

Aluminum is highly advantageous from a number of standpoints. It is quite readily available in the desired quantities, it is easily fabricated, it has great strength, and it is most effective in gripping the patient's hand and holding it in the desired, straight position.

Another advantage of utilizing aluminum to form the immobilizer is that aluminum is more environmentally friendly than lead or other materials and it can be disposed of in the general articles of waste. Lead, under the rules of careful handling, should not be thrown in the normal waste, but should be handled separately for disposal. As contrasted with that, aluminum can be easily recycled, and therefore can be disposed of in normal trash.

Another and most important feature is that aluminum enables x-rays to the be taken of the patient's hand, where and contrast to that, such x-rays could not be taken through lead.

BRIEF DESCRIPTION OF THE INDIVIDUAL FIGURES OF THE DRAWINGS

FIG. 1 is a face view of the back side of the immobilizer, showing the aluminum.

FIG. 2 is a face view of the front side, showing the cushion layer.

FIG. 3 is a face view of the patient's hand with the immobilizer applied thereto.

FIG. 4 is a fragmentary view taken at line. 4—4 of FIG. 3.

FIG. 5 is a large scale sectional view taken at line 5—5 of FIG. 2.

FIG. 6 is a perspective view of sheets of aluminum and cushion material, in aggregate form, and indicating the method of forming the final article.

FIG. 7 is a view of the layers of FIG. 6 fitted together, the layers being shown together with a cutter for cutting through the combination of the layers to form the final article.

FIG. 8 is a perspective view at an angle, from the side, of the finished article.

DETAILED DESCRIPTION OF THE DRAWINGS

Attention is directed first to FIGS. 1 and 2 which show the immobilizer or device of the invention in complete form. FIG. 1 shows the back side and FIG. 2 shows the front side.

For convenience, and simplicity in referring to the immobilizer, it may be referred to as an article.

The entire article is indicated at 10 and includes two layers, a layer of aluminum 12 and a layer of sponge material 14 forming a cushion. In fabricating the device, two sheets of those materials, 12a, 14a, in aggregate shape and form, are provided as shown in FIG. 5. The sheets may be of rectangular shape, and are continuous and uniform throughout their area within their outline shape. They are glued together by a suitable glue 16, which is spread throughout the area of the sheet 12a, so that in the finished article it is spread throughout the interengaging areas of the two layers.

The final article or product is shaped as shown in FIGS. 1 and 2, and includes a main segment 18 corresponding to the main part of the hand, or metacarpus; it also includes digital segments 20 corresponding to the fingers of the hand, and side tab segments 22 to be identified in detail hereinbelow.

For purposes of identification and clarification, the elements of the patient's body concerned herein are: the limb, includes the full arm, including the full hand; the arm, extends down to and includes the wrist; the hand, is the portion outwardly of the wrist; all of the fingers together are identified as digits; those fingers other than the thumb may also be referred to as fingers, to distinguish them from the thumb.

For further simplification of reference to the device, the device is considered as having an inner or rear end 24 and an outer or front end 26. The side tab segments 22 include a first pair 22a and 22b extending laterally outward at the rear end of the article, these tabs and the remainder of the article together having a common straight transverse border line 25 the rear end of the device; the side tab segments a so include a second pair 22c, 22d extending generally outwardly, forwardly of the segments 22a, 22b, although at a different angle. The side tab segments 22c, 22d may extend generally perpendicularly from the adjacent digits, which places them in a different angle, referred to above, from the segments 22a, 22b.

The article is applied to the patient's hand 23 as represented in FIGS. 2 and 3. In FIG. 2, the front side, or cushioned side, is shown, and the patient's hand is placed in position shown in FIG. 3, with palm side up. Then the side tab segments 22 are bent up and over the corresponding elements of the limb. The innermost segments 22a, 22b are positioned adjacent the wrist of the patient and are therefore folded over the wrist.

The hand of the patient assumes a larger transverse dimension, outwardly of the wrist, as indicated at 27, just rearwardly of the thumb. The tab segments 22a, 22b are positioned inwardly from that large portion, and thus they snugly hold the article from moving or sliding off the hand, in outward direction.

The other pair of tab segments, 22c, 22d, are positioned at the main part of the hand, and are bent up and over that main part of the hand, these segments thereby holding the article against sideways movement.

The article is of sufficient size that when it is applied to the hand, the ends of the digits of the hand do not reach out to the ends 26 of the digital segments 20, and the ends of the those digital segments are then bent over the ends 25 of the digits as shown in FIGS. 3 and 4. These end portions hold the article on the hands relative to the ends of the fingers.

The tabs formed by the digital extensions are of substantial size, so as to extend back (FIG. 4) from the ends of the digits a substantial distance for covering substantial portions of the digits.

The aluminum layer is of relatively great strength so that forces such as those tending to double up the hand, will not deflect those tabs, so as to enable the fingertips to be released. While the dimension of the aluminum layer may be any within a substantial, range, it is found that a thickness of 0.034" is satisfactory. A sponge layer 4 may be for example of 0.7/32" in thickness. As will be obvious, these dimensions are not limiting, but indicative.

FIG. 7 indicates the final step in fabricating the article. It is preferred that the layers of aggregate material (FIG. 6) be glued together and the cutting done afterward. FIG. 7 shows a cutter 28 shaped according to the desired final article, which is utilized for cutting through the combination of layers, the aluminum and the sponge material. This method is a great advantage in producing an a curate fitting together of the two layers, and the ease in doing so, in addition to presenting a trim appearance.

The article can be removed from the patient's hand quite readily, by releasing the tabs by gripping them and bending them back toward straight position.

I claim:

1. An article constituted by a patient's hand immobilizer, the hand constituting the terminal portion of the limb, comprising, a rigid panel to be fitted to the hand and having an inner end and an outer end, the panel being integral and of one-piece of aluminum, and being planar in shape, and of uniform thickness throughout its outline dimensions, the panel including
    a) a main segment shaped to the metacarpus,
    b) digital segments shaped to the fingers respectively and positioned correspondingly thereto, and
    c) a first pair and a second pair of side tab elements, said side tab elements extending laterally outwardly from the main segment of the article, the first pair of side tab elements being at the extreme inner end of the article and thereby inwardly of the position of the widest part of the hand and adjacent the wrist, the second pair of side tab elements being forwardly of the first pair and adjacent the forward end of the main segment, a layer of sponge material of the same size and shape as the aluminum layer and secured to the latter, and the digital segments and the side tab elements having free outer end portions bendable over the corresponding portions of the hand operable for securing the article on the hand.

2. An article according to claim 1 wherein, the aluminum panel is in the neighborhood of 0.034" thick.

3. A method of making a patient's hand immobilizer, having various elements dimensioned and shaped according to corresponding elements on the hand, comprising, providing a sheet of aggregate aluminum material and a sheet of aggregate sponge material, both larger that the intended immobilizer, and both continuous and uniform in thickness throughout their outline dimensions, securing the sheets together throughout their interengaging areas, thereby forming a compound article which is consequently of aggregate character, and cutting from that compound article a piece which forms the immobilizer.

\* \* \* \* \*